United States Patent [19]

Miller et al.

[11] Patent Number: 5,169,869
[45] Date of Patent: Dec. 8, 1992

[54] PROCESS FOR PRODUCING HIGHER ALCOHOLS OR N-PARAFFINS FROM SYNTHESIS GAS

[75] Inventors: Jeffrey T. Miller, Naperville, Ill.; Thomas D. Nevitt, deceased, late of Corrales, N. Mex., by Norma J. Nevitt, legal representative

[73] Assignee: Amoco Corporation, Chicago, Ill.

[21] Appl. No.: 725,569

[22] Filed: Jul. 3, 1991

Related U.S. Application Data

[63] Continuation-in-part of Ser. No. 466,071, Jan. 16, 1990, abandoned.

[51] Int. Cl.$^5$ .......................... C07C 1/04; C07C 27/06
[52] U.S. Cl. ...................................... 518/713; 502/318
[58] Field of Search ........................................ 518/713

[56] References Cited

U.S. PATENT DOCUMENTS

| | | |
|---|---|---|
| 1,746,782 | 2/1930 | Lazier . |
| 1,746,783 | 2/1930 | Lazier . |
| 1,824,896 | 9/1931 | Jaegar . |
| 1,859,244 | 5/1932 | Patart . |
| 2,110,483 | 3/1938 | Guyer ............................ 260/156 |
| 2,241,416 | 5/1941 | Normann ........................ 260/638 |
| 2,960,518 | 11/1960 | Peters ........................... 260/449.6 |
| 3,925,490 | 12/1975 | Reich et al. ................... 260/643 B |
| 4,122,110 | 10/1978 | Sugier et al. ................. 518/713 |
| 4,237,063 | 12/1980 | Bell et al. ..................... 260/449 R |
| 4,298,354 | 11/1981 | Hardman et al. ............. 44/56 |
| 4,451,579 | 5/1984 | Lemanski et al. ............ 502/306 |
| 4,477,594 | 10/1984 | Greene et al. ................ 518/700 |
| 4,478,955 | 10/1984 | Pesa et al. .................... 518/713 |
| 4,559,316 | 12/1985 | Mazanec et al. ............. 518/713 |
| 4,576,968 | 3/1986 | Nay et al. ..................... 518/713 |
| 4,613,707 | 9/1986 | Kouba et al. ................. 568/864 |
| 4,751,248 | 6/1988 | Lin et al. ...................... 518/707 |
| 4,843,101 | 6/1989 | Klier et al. ................... 518/713 |
| 5,004,845 | 4/1991 | Bradley et al. ............... 568/885 |
| 5,021,233 | 6/1991 | Klier et al. ................... 423/656 |

FOREIGN PATENT DOCUMENTS

| | | | |
|---|---|---|---|
| 738487 | 7/1966 | Canada ......................... | 260/722 |
| 272555 | 1/1929 | United Kingdom .......... | 518/713 |

OTHER PUBLICATIONS

Monnier, et al., *Journal of Catalysis*, vol. 92, pp. 119–126 (1985).
Emmett, ed., *Catalysis*, vol. V, pp. 131–1745 (1957).
Tahara, et al., J. Soc. Chem. Ind. (Japan), vol. 43, 82 B (1940).
Tahara, et al., J. Soc. Chem. Ind. (Japan), vol. 45, Suppl. Bind. 89 (1942)—Partial Translation.

*Primary Examiner*—Howard T. Mars
*Attorney, Agent, or Firm*—Nick C. Kottis; Scott P. McDonald; Frank J. Sroka

[57] ABSTRACT

A process for converting synthesis gas to n-paraffins or higher alcohols utilizes a mixed copper-chromium oxide catalyst. The process allows great flexibility in selecting the product mix by changing catalyst compositions and process conditions.

35 Claims, No Drawings

PROCESS FOR PRODUCING HIGHER ALCOHOLS OR N-PARAFFINS FROM SYNTHESIS GAS

This is a continuation-in-part of copending, commonly assigned application Ser. No. 07/466,071 filed Jan. 16, 1990, now abandoned, the disclosure of which is incorporated herein by reference.

BACKGROUND OF THE INVENTION

1. Field of the Invention

This invention relates generally to synthesis gas conversion and, more specifically, this invention relates to a catalyst and process for selectively converting synthesis gas to n-paraffins or higher alcohols.

2. Brief Description of Related Technology

Large reserves of natural gas or methane are located in remote areas of the world. As oil reserves are depleted, there is great incentive to convert this gas into a commodity liquid fuel. A number of direct methane conversion technologies, such as pyrolysis, oxidative coupling, and direct oxidation exist, but are in the early stages of development. However, there are well-established technologies for the conversion of natural gas into synthesis gas, i.e., a mixture of CO and free molecular hydrogen.

The Fischer-Tropsch process is a well-known synthesis gas reaction for making hydrocarbons. The economics of the Fischer-Tropsch process have been investigated periodically and have generally been found to be unfavorable. The direct synthesis of higher alcohols (i.e., those having 2 or more carbon atoms per molecule) from carbon monoxide and hydrogen has attracted attention because the products are suitable as gasoline extenders and high-octane blending components.

The formation of aliphatic alcohols by the hydrogenation of carbon monoxide is represented by the following equations:

$$2n\, H_2 + n\, CO \rightarrow C_nH_{2n+1}OH + (n-1)\, H_2O \quad [1]$$

$$(n+1)\, H_2 + (2n-1)\, CO \rightarrow C_2H_{2n+1}OH + (n-1)\, CO_2 \quad [2]$$

The water-gas shift reaction [3, below] is closely linked to the alcohol synthetic reaction:

$$CO + H_2O \rightarrow CO_2 + H_2 \quad [3]$$

The hydrogenation of carbon monoxide to hydrocarbons is thermodynamically more favorable than hydrogenation to alcohols; thus, alcohol formation requires selective catalysts in order to minimize hydrocarbon formation.

Catalysts for higher alcohol processes which have reached the commercialization stage or have undergone large-scale pilot plant trials fall into three main categories. They include low temperature methanol synthesis catalysts modified with alkali metals, high temperature methanol synthesis catalysts modified with alkali metals, and modified Fischer-Tropsch catalysts.

Low temperature methanol synthesis catalysts which have been modified for higher alcohol synthesis by the addition of alkali metals usually contain both copper and zinc and may contain oxides of chromium or aluminum. The product of one such catalyst typically contains 50-70 percent methanol (depending on the $H_2$:CO ratio of the synthesis gas feed), the balance being $C_2$-$C_8$ alcohols and partially hydrogenated oxygenates. The water content can be reduced to a few percent, while the content of light hydrocarbons is negligible. Typical reaction conditions are 1,500 psig and 520° F. The main shortcomings of this type of higher alcohol catalyst include the presence of a high fraction of methanol in the product, sensitivity of the catalyst to the carbon dioxide level, increased light hydrocarbon production, and deterioration of catalyst activity with time, especially when operated at relatively high temperatures.

High temperature methanol synthesis catalysts which have been modified with alkali metals to produce higher alcohols usually contain ZnO and $Cr_2O_3$ and may also contain oxides of copper. Typical processes of this type operate at $H_2$:CO ratios of 0.5-3, a temperature of 625-800° F., a pressure of 1,300-2,600 psig, and a gas hourly space velocity (GHSV) of 3,000-15,000/hr. The alcohol product is about 70 percent methanol, with the remainder being $C_2$-$C_5$+ higher alcohols and oxygenates. Isobutanol is the principal higher alcohol. At these conditions water can be about 20 percent of the crude product, and hydrocarbon contents are low. The catalysts are quite stable with time. Main drawbacks include the presence of a large amount of methanol in the product, the need to remove large amounts of water, the need to use a synthesis gas feed with a low $H_2$:CO ratio, and a high operating pressure.

One example of a modified Fischer-Tropsch catalyst contains $MoS_2$, CoS, and $K_2O$. This catalyst has been reported to yield about 85 percent mixed alcohols, with the remainder as $C_1$-$C_5$ paraffins.

The crude mixed alcohol product of this type of catalyst contains about 50 percent methanol, with the remainder $C_2+$ alcohols and oxygenates. Ethanol is the major higher alcohol. This catalyst effects a water-gas shift reaction at alcohol synthesis conditions and thus provides a product with less than about 3 percent water. One drawback to this process can be a high yield of light hydrocarbons. The catalyst is believed to require 25-50 ppm $H_2S$ in the feed gas to maintain acceptable activity.

The preparation of alcohols from carbon monoxide and hydrogen yields a range of alcohol chain lengths as well as linear or branched alcohols. Generally, higher alcohols which form over copper-containing catalysts are branched; those formed over Group VIII metals are predominately straight-chained.

Mixed copper-cobalt alkalized catalysts have been developed by Institut Francais du Petrole for conversion of synthesis gas to higher alcohols. These catalysts generally also contain aluminum, chromium, and zinc. Although these catalysts contain both copper (a component of many methanol synthesis catalysts) and cobalt (a typical Fischer-Tropsch catalyst component), the product distribution is similar to that obtained from a modified Fischer-Tropsch catalyst, i.e., ethanol is the major $C_{2+}$ alcohol. A typical product from such a catalyst would comprise, on a $CO_2$-free basis, 70-80 percent oxygenates and 20-30 percent hydrocarbons. Of the oxygenates, methanol can be 50-70 percent, ethanol 16-25 percent, and the balance other alcohols and partially hydrogenated oxygenates. Such catalysts typically operate at 500 to 600° F., 1000-1500 psig, and a GHSV of 3000-6000/hr, an $H_2$:CO molar ratio of 2 or less, and $CO_2$ content in the feed gas of less than 3 percent. Drawbacks include the high methanol fraction in the alcohol product and the large amount of light hydrocarbons that are also produced. The performance of this type of copper-cobalt catalyst is especially sensitive to the method by which it is prepared. Large-scale industrial preparation may need very tight controls to ensure an active material.

SUMMARY OF THE INVENTION

It is an object of the invention to overcome one or more of the problems described above.

According to the invention, a process for converting synthesis gas is provided wherein synthesis gas is contacted with a mixed copper-chromium oxide conversion catalyst under conditions whereby at least a portion of the synthesis gas is converted to n-paraffins or higher alcohols.

The inventive process may provide a relatively dry single phase liquid product which is relatively lean in non-alcohol oxygenates.

The invention also comprehends a catalyst useful in the inventive process.

Other objects and advantages of the invention will be apparent to those skilled in the art from a review of the following detailed description taken in conjunction with the appended claims.

DETAILED DESCRIPTION OF THE INVENTION

According to the invention, methanol and n-paraffins (e.g., paraffins having 1-15 or more carbon atoms per molecule) or methanol and higher alcohols (i.e., those containing at least 2 carbon atoms per molecule) may be efficiently produced in high yield from synthesis gas in a catalytic reaction system. In the inventive system, synthesis gas is contacted with a mixed copper-chromium oxide catalyst under suitable conditions in order to convert at least a portion of the synthesis gas to higher alcohols or n-paraffins.

The composition of the feed synthesis gas can vary widely, and generally comprises $H_2$ and CO in an $H_2:CO$ molar ratio in the range of about 5:1 to about 1:5, preferably in the range of about 1:1 to about 2:1. Preferably, the feed synthesis gas also comprises about 2 to 20 volume percent $CO_2$.

$CO_2$ is known to increase the reaction rate of copper synthesis gas conversion catalysts. It is believed that $CO_2$ may be a reactive species, rather than or in addition to CO. Alternatively, it is speculated that $CO_2$ maintains the copper is a catalytically active state.

The synthesis gas conversion reaction is preferably carried out at a temperature in the range of about 500° F. to about 700° F. A reaction pressure of at least about 500 psig, preferably at about 500 to 1500 psig (or more) is preferred for the production of n-paraffins. For the production of higher alcohols, the reaction is carried out at a pressure of greater than about 1500 psig, preferably about 1750 to 2000 psig.

The preferred temperature range for both reactions depends on the specific activity of the catalyst. The preferred temperature range for n-paraffin production is 525°-600° F. and for higher alcohols the preferred temperature is 550°-700° F.

An important role of the catalyst is to convert a portion of any undesirable unsaturated oxygenate intermediates to alcohols by hydrogenation and to reduce the water content of the liquid product by means of a water-gas shift reaction.

As used herein, the term "oxygenates" includes alcohols, and the term "unsaturated oxygenates" denotes non-alcohol oxygenates such as carboxylic acids, aldehydes, ketones, and esters.

Descriptions herein of the catalyst-forming components used according to the invention are made with reference to the state of the catalyst prior to reduction under operating conditions unless otherwise specified.

The copper-containing catalyst is free or substantially free of cobalt and/or ZnO, as well as other catalytically active species other than copper and chromium and the alkali metal promoter, and is selected in part for its ability to hydrogenate unsaturated organic oxygenates and to effect a water-gas shift reaction. Prior combinations of copper and zinc which are known to produce alcohols or, in combination with alkali metals to produce higher alcohols do not effect an efficient water-gas shift reaction under alcohol synthesis conditions.

The inventive process, on the other hand, efficiently produces relatively dry higher alcohols due to a simultaneous water-gas shift reaction under alcohol synthesis conditions.

Copper is known to be a hydrogenation catalyst, especially for oxygenates, and the preferred form of copper in the catalyst is Cu(II) (prior to partial reduction under conversion conditions). For use in production of higher alcohols, the catalyst may contain alkali metal compounds which serve to suppress methanol synthesis activity and promote higher alcohol selectivity. At least trace amounts (e.g. up to about 1 wt. %, typically in the range of about 0.2 to 0.7 wt. % and preferably at least about 0.1 wt. %, measured as carbonate, i.e. $K_2CO_3$) of an alkali metal compound should be present for the production of n-paraffins.

The catalyst is generally characterized as a non-stoichiometric mixed copper-chromium oxide which is prepared by coprecipitation, with optional subsequent impregnation with a solution of an alkali metal salt, especially if the catalyst is to be used for higher alcohols production. The coprecipitated mixed copper-chromium oxide catalyst (with or without alkali metal) is referred to as a "copper chromite" catalyst.

Preparation of the copper chromite catalyst is effected by coprecipitating copper (II) ions with chromate ions in the presence of a molar excess of ammonium relative to copper to produce a copper-ammonium-chromate precipitate. This precipitate is believed to comprise a copper (II)-ammonium complex coordinated to chromate (i.e. Cr (VI) oxide). Coprecipitation may be conveniently effected by mixing respective solutions of copper nitrate ($Cu(NO_3)_2$) or another soluble copper (II) salt and a stoichiometric excess of a solution of ammonium chromate ($(NH_4)_2CrO_4$) with at least a 3:1 weight ratio of ammonium chromate to copper nitrate. If desired, ammonium hydroxide or an equivalent soluble ammonium salt can be partially substituted for ammonium chromate.

When the catalyst is to be used in the conversion of synthesis gas to n-paraffins, it is preferred that a small amount of an alkali metal chromate (e.g. potassium chromate, $K_2CrO_4$) be partially substituted for ammonium chromate in order to provide a trace amount (i.e. less than about 1 wt. %, typically in the range of about 0.2 to about 0.7 wt. % and preferably at least about 0.1 wt. %, measured as carbonate) of alkali metal to the catalyst in order to increase the selectivity of the catalyst for n-paraffins. Alternatively, the catalyst may be impregnated with a small amount of an alkali metal compound as described below.

Precipitation of the copper-ammonium-chromate precipitate is effected by mixing of the two (i.e., copper nitrate and ammonium chromate) solutions. If ammonium hydroxide is to be present, it can be mixed with the ammonium chromate solution prior to mixing with the copper nitrate solution. The precipitate is separated from the mixture and dried by any suitable nondegradative means (e.g. by filtering and vacuum drying) to produce a product which is typically brown in color.

The copper content of catalysts prepared by simple precipitation of copper nitrates or similar salts may vary widely, with typical copper contents (calculated as CuO) of about 10 wt. % to about 60 wt. %. Copper chromite catalysts made as described above generally contain copper and chromium in a $CuO:Cr_2O_3$ weight ratio of about 0.5:1 to about 1.5:1, typically about 0.8:1 to 1.2:1.

The precipitate is then calcined under carefully controlled temperature conditions to drive off ammonium ions to form a stable, mixed copper (II)/chromium (III) oxide ("copper chromite") catalyst which is typically black. The calcining step is carried out at a sufficiently high temperature to drive off ammonia and fix the CuO and $Cr_2O_3$ constituents of the copper chromite catalyst. The temperature is controlled so as not to reach a temperature at which the surface and catalytic properties of the catalyst degrades. A calcining temperature of about 525° F. to about 575° F. or less is preferred, although a 600° F. temperature may be used as long as spikes in temperature above 700° F. are avoided. (Slightly higher temperatures may be used if certain other components such as BaO are present.)

In general, the activity of the catalyst decreases as the calcination temperature increases.

Activity may be maximized, at least in some cases, by a multi-step calcination procedure wherein a first, relatively low temperature calcination step is done near, or slightly below, the decomposition temperature of the copper-ammonium-chromate to the black copper chromite, followed by a second, higher temperature calcination step. For example, the brown copper-ammonium-chromate may be calcined at about 400° to about 450° F., followed by a second calcination at about 500° to about 650° F., preferably about 575° to about 625° F., e.g. 610°.

The low temperature calcination step at near the copper-ammonium-chromate decomposition temperature promotes the desirable structural change, which is exothermic in nature, without undesirable sintering or other adverse effects.

It is preferred to wash the copper-ammonium-chromate precipitate to remove soluble unreacted materials and by-products prior to drying and calcining in order to maximize activity. Washing is conveniently carried out with water.

If intended for use in producing higher alcohols, after calcining the copper chromite catalyst is impregnated with a preferably aqueous solution of a soluble alkali metal compound, and dried by calcining to provide an alkali-impregnated copper chromite catalyst. Temperature control of this calcining step is less important than control of the initial calcining step and this calcining step is preferably conducted at temperatures of up to 650° F., such as 625° F.

The alkali metal compound, if present, preferably comprises between about 1 and about 10 wt. % of the catalyst (measured as carbonate) when the catalyst is to be used for higher alcohol production. In such case, the alkali metal compound is preferably present at about a 5 wt. % level.

Of the alkali metals, potassium and sodium are preferred, although cesium and rubidium are acceptable. The alkali metal compound preferably is a potassium salt such as KOH or the highly preferred $K_2CO_3$.

The catalyst may contain other components, as desired. Barium (in oxide form, BaO) is a useful additional component, especially in copper chromite catalysts. The presence of a soluble barium salt in the catalyst-forming solution facilitates copper chromite precipitation, and results in the formation of stable barium chromite which enhances the physical strength of the catalyst without detrimentally affecting catalyst performance.

The active species of the catalyst preferably consist essentially of, and highly preferably consist of the non-stoichiometric mixed copper-chromium oxide and alkali metal compound, and the catalyst is preferably free or substantially free of cobalt, zinc and other catalytically active species, including, without limitation, iron, titanium, vanadium, rhenium, catalytically active manganese, platinum, palladium, rhodium, nickel, molybdenum, tungsten, ruthenium, and catalytically active metals selected from Groups IVB, V, VII or VIII of the Periodic Table. Non-catalytic materials, such as aluminum and silicon, clays, high surface area carbon, and zeolites, for example, used in some syngas conversion catalysts of the prior art are not required, although they may be present to enhance physical properties of the catalyst, if desired.

The term "substantially free" of cobalt, and other catalytic species, such as highly active iron, rhenium, nickel, molybdenum, tungsten, and ruthenium denotes that such species should not be present in amounts which materially affect the catalytic composition of the invention. More specifically, such materials, although they may be present in trace or small amounts (i.e. up to about 0.1 wt. %, preferably less than about 0.01 wt. % of the catalyst, measured as oxide) insufficient to affect the catalytic composition, should not be present in amounts which measurably affect the nature of level of activity of the catalyst, or which measurably change the selectivity thereof.

When copper chromium catalysts are made according to the inventive procedure, the presence of zinc or the remaining species identified above in the catalyst is neither beneficial nor harmful at concentrations of up to about 5 wt. %, measured as oxide.

Stated somewhat differently, copper and chromium, taken in combination with the alkali metal promoter are preferably substantially the only catalytically active species present in the catalyst.

When synthesis gas is passed over a bed of the catalyst under conversion conditions, a liquid product is obtained upon cooling of the gaseous effluent, and typically forms a single liquid phase. The production of a single phase establishes that the catalyst effects a water-gas shift reaction to minimize the water present in the product. Single phase liquid products of the inventive process will generally contain less than about 10 vol. % water.

The catalytic process of the invention yields optically clear, colorless material which is oxidatively stable when exposed to air over lengthy time periods. This phenomenon may be explained on the basis that copper in the catalyst hydrogenates product constituents which cause color formation upon oxidation, such as by-product acids, aldehydes, ketones, and esters.

EXAMPLES

The following specific examples are provided in order to illustrate the practice of the invention, but are not to be construed to limit the scope of the invention. In the following examples, all percentages are expressed in terms of weight unless specified otherwise.

EXAMPLE 1

Catalyst Preparation

Catalyst A 75.0 g of ammonium chromate, $(NH_4)_2CrO_4$, was dissolved in 100 ml $H_2O$. Separately, 25.0 g of copper nitrate, $Cu(NO_3)_2.3H_2)$, was dissolved in 25 ml $H_2O$. The two solutions were mixed rapidly to from a brown precipitate. The precipitate was filtered and dried under vacuum at 110° C. The brown solid was calcined at 475° F. for 2 hours. The final catalyst was black.

Catalyst B 75.0 g of ammonium chromate, $(NH_4)_2CrO_4$, was dissolved in 75 ml $H_2O$. Separately, 25.0 g of copper nitrate, $Cu(NO_3)_2.3H_2O$, was dissolved in 25 ml $H_2O$. The two solutions were rapidly mixed to form a brown precipitate. The precipitate was filtered and vacuum dried at 110° C. The powder was heated to 400° F., where the solid turned black. The catalyst was further heated at 600° F. for 1 hour.

Catalyst C 100 g of $(NH_4)_2CrO_4$ was dissolved in 100 ml $H_2O$. A few drops (~.5 ml) of $NH_4OH$ was added to the $(NH_4)CrO_4$ solution. Separately, 25 g of $Cu(NO_3)_2.3H_3O$ was dissolved in 25 ml $H_2O$. The two solutions were mixed rapidly to form a brown precipitate. The solid was dried under vacuum at 110° C. and calcined for 2 hours at 475° F. The final catalyst was black.

Catalyst D 75 g of $(NH_4)CrO_4$ was dissolved in 75 ml $H_2O$. 3 drops of $NH_4OH$ were added to the $(NH_4)_2CrO_4$ solution. Separately, 25 g of $Cu(NO_3)_2.3H_2O$ was dissolved in 25 ml $H_2O$. The two solutions were rapidly mixed to precipitate a brown solid. The solid was filtered, reslurried in 100 ml $H_2O$, stirred for 10 minutes and refiltered. The solid was washed a second time in 100 ml $H_2O$ and refiltered. The solid was dried under vacuum at 110° C. The brown solid was calcined at 475° F. for 1 hour and 525° F. for 1 hour.

Catalyst E 75.0 g of $(NH_4)_2CrO_4$ was dissolved in 75 ml $H_2O$. A few drops of $NH_4OH$ (0.5 ml) were added to the $(NH_4)_2CrO_4$ solution. Separately, 25 g of $Cu(NO_3)_2.3H_2O$ was dissolved in 25 ml $H_2O$. The two solutions were mixed rapidly to form a brown precipitate. The solid was filtered. The brown catalyst was washed twice by adding 200 ml $H_2O$ and stirring. The washed catalyst was filtered, dried under vacuum at 110° C. and calcined at 525° F. for 1 hour.

Catalyst Testing 1.0 g each of Catalysts A through E was loaded into a 500 ml static autoclave. The autoclave was pressurized and sealed with synthesis gas. The gas composition was 65.6 vol % $H_2$, 29.3 vol. % CO and 5.1 vol. % $CO_2$.

The reactor was heated to 600° F. where the initial pressure was approximately 2200 psig. The sample was allowed to react overnight (17 hours). The products were collected by venting the reaction mixture slowly through a dry ice trap. For all catalysts the reaction product was methanol. The yields of methanol for each catalyst are given in Table I. Catalysts C, D and E were much more active than Catalysts A and B.

TABLE I

EFFECTS OF AMMONIUM HYDROXIDE ADDITION AND WASHING ON CATALYST ACTIVITY

| Catalyst | $NH_4OH$ | Wash | Yield (ml/17 hrs) |
|---|---|---|---|
| A | No | No | 0.2 |
| B | No | No | 1.3 |
| C | Yes | No | 5.8 |
| D | Yes | Yes | 9.6 |
| E | Yes | Yes | 10.0 |

EXAMPLE 2

The Effect of Alkali on Activity and Selectivity

Catalysts C and E were impregnated with $K_2CO_3$ to add 8 wt. % $K_2CO_3$ to the catalyst. For example, 20.0 g of Catalyst C was impregnated with 1.6 g $K_2CO_2$ dissolved in 15 ml $H_2O$. The $H_2O$ was evaporated under vacuum and the dried catalyst was calcined at 600° F. for 1 hour. Catalyst C containing alkali is designated Catalyst F. Similarly, Catalyst E containing alkali is designated Catalyst G.

1.0 g of each of Catalysts F and G was retested with synthesis gas in a static autoclave as described in Example 1. The results are given in Table II. For both catalysts, alkali addition substantially decreased the synthesis gas conversion resulting in lower methanol yields. In order to obtain reasonable product yields with alkali promoted catalysts, very active non-alkali catalysts are required.

TABLE II

EFFECT OF ALKALI METAL IMPREGNATION (8 WT % $K_2CO_3$) ON METHANOL YIELD

| Alkali Catalyst | Before Alkali Addition (ml/17 hrs) | After Alkali Addition (ml/17 hrs) |
|---|---|---|
| F | 5.8 | 0.75 |
| G | 10.5 | 2.0 |

Catalysts F and G were further tested for alcohol synthesis in a fixed-bed, continuous-flow pilot plant under the conditions shown in Table III. Yields were determined by gas chromatography. The flow rate was controlled by mass flow controllers and metered from the test unit by a wet test meter. The gas flow rate (cc of gas per gram of catalyst per hour) and carbon monoxide analysis were determined prior to reaction and again at the reaction temperature. The liquid products were collected for about 24 hours and analyzed by gas chromatography. The results are presented in Table III.

TABLE III

| Catalyst: | F | G |
|---|---|---|
| Temp, °F. | 645 | 625 |
| Pressure (psig) | 1500 | 1500 |
| Inlet GHSV (cc/hr-g cat) | 2270.9 | 1624 |
| vol. % CO | 48. | 48.1 |
| vol. % $CO_2$ | 8.5 | 8.6 |
| Outlet GHSV (cc/hr-g cat) | 2107.5 | 1346.2 |
| vol. % CO | 48.4 | 48.1 |

TABLE III-continued

| Catalyst: | F | G |
|---|---|---|
| vol. % $CO_2$ | 10.2 | 12.3 |
| Selectivity (wt. %) | | |
| $CO_2$ | 26.8 | 20.2 |
| MeOH | 40.6 | 43.7 |
| $C_2^+$ Alcohol | 7.5 | 9.2 |
| HC | 25.0 | 26.9 |
| CO conversion (%) | 7.0 | 17.1 |
| Yield (g/hr/g cat) | | |
| HC | .012 | .023 |
| MeOH | .045 | .082 |
| $C_2^+$ Alcohol | .006 | .012 |
| Wt % $C_2^+$ Alcohol | 15.9 | 15.9 |

Table III demonstrates that alkali promoted copper chromite catalysts produce $C_2+$ alcohols. For example, under the tested conditions both catalysts produced approximately 15% higher alcohols. In addition, despite a 25° F. lower operating temperature, Catalyst G had twice the activity of Catalyst F, giving twice the yield of products. The most active alkali promoted catalyst (Catalyst G) was produced from the most active alkali-free copper chromite catalyst (Catalyst E).

EXAMPLE 3

Hydrocarbon (n-Paraffin) Synthesis with Copper Chromite Catalysts

Catalyst H 60 g of $(NH_4)_2CrO_4$ was dissolved in 150 ml $H_2O$. Separately, 20.0 g of $Cu(NO_3)_2.3H_2O$ was dissolved in 30 ml $H_2O$. The two solutions were mixed rapidly to precipitate a brown solid. The solid was filtered and washed with 25 ml $H_2O$ and dried. The catalyst was calcined at 400° F. for 2 hours and an additional hour at 700° F.

Catalyst I 26 01 g of $Ba(NO_3)_2$ was dissolved in 800 ml $H_2O$ and heated to 150° F. 218.12 g $Cu(NO_3 2.3H_2O$ was added. A separate solution of ammonium chromate was prepared by dissolving 126.02 g $(NH_4)_2Cr_2O_7$ in 600 ml $H_2O$ and adding 150 ml $NH_4OH$ The two solutions were rapidly mixed. The resulting solid precipitate was filtered and washed twice, each time with 200 ml $H_2O$. The washed solid was dried overnight at 250° F. in a vacuum oven. The resulting catalyst was slowly heated to 600° F. and maintained at that temperature for one hour. The resulting barium-copper chromite catalyst was analyzed to contain 37.6 wt. % CuO, 48.2 wt. % $Cr_2O_3$, and 8.9 wt. % BaO, the balance comprising water, other carbonates, and other oxides.

Catalyst J 40.0 g $(NH_4)_2CrO_4$ was dissolved in 80 ml $H_2O$. Separately, 25 g of $Cu(NO_3)_2.3H_2O$ was dissolved in 25 ml $H_2$.. The solutions were mixed, and the resulting precipitate was filtered, washed with 25 ml $H_2O$, and dried. The catalyst was calcined at 400° F. for 2 hours and at 700° F. for 1 hour.

Catalyst K 70.0 g of $(NH_4)_2CrO_4$ and 5.0 g of $K_2CrO_4$ were partially dissolved in 75 ml $H_2O$. Separately, 25.0 g $Cu(NO_3)_2.3H_2O$ was dissolved in 25 ml $H_2O$. The two solutions were rapidly mixed to form a precipitate. The precipitate was filtered and washed with 25 ml $H_2O$, dried at 110° C. and calcined at 425° F. for 1 hour.

Catalyst L 74.5 g of $(NH_4)_2CrO_4$ and 0.82 g $K_2CrO_4$ were partially dissolved in 75 ml $H_2O$. Separately, 25.0 g Cu(-$NO_3)_2.3H_2O$ was dissolved in 25 ml $H_2O$. The two solutions were mixed rapidly. The precipitate was filtered and washed with 25 ml $H_2O$. The dry catalyst was calcined at 600° F. for 2 hours.

Testing Procedure

Catalysts H through L were tested for synthesis gas conversion in a fixed-bed, continuous-flow pilot plant under the conditions shown in Tables IV and V. Yields were determined by gas chromatography. The flow rate was controlled by mass flow controllers and metered from the test unit by a wet test meter. The gas flow rate (cc of gas per gram of catalyst per hour) and carbon monoxide analysis were determined prior to reaction and again at the reaction temperature. The liquid products were collected for about 24 hours and analyzed by gas chromatography.

The catalysts were tested at two different operating pressures, low pressure (500 psig) and high pressure (greater than 1000 psig). The results of the low pressure tests are given in Table IV, and the results of the high pressure tests are given in Table V.

From Table IV, it can be seen that each of the copper chromite catalysts tested at 500 psig produced only single carbon products, for example, methanol or methane. Dimethyl ether (DME) results from the acid catalyzed dehydration of methanol. On the other hand at reaction pressures above 1000 psig, Table V, the tested copper chromite catalysts produce n-paraffins; i.e. products with carbon-carbon bonds.

Catalysts with low levels of alkali metal (<1 wt. % $K_2$), Catalysts K and L) are more selective for n-paraffin synthesis than catalysts free of alkali (Catalyst H, for example). The Schultz-Flory coefficient for all copper chromite catalysts is approximately 0.45. n-paraffin products containing 20 carbon atoms have been detected, at low concentrations.

TABLE IV

| | SYNGAS REACTIONS AT 500 PSIG and 565° F. WITH COPPER CHROMITE | | | | | | | | | | |
|---|---|---|---|---|---|---|---|---|---|---|---|
| | Inlet | | | Outlet | | | | Yield | | Selectivity | |
| Catalyst | GHSV hr$^{-1}$ | vol. % CO | vol. % $CO_2$ | GHSV hr$^{-1}$ | vol. % CO | vol. % $CO_2$ | CO Conversion, % | g/hr/g cat MeOH | $CO_2$ | $CH_4$ | DME | $CH_3OH$ |
| H | 3662 | 31.01 | 1.96 | 3313 | 29.78 | 2.34 | 13.1 | 0.22 | 3.4 | 2.9 | 19.5 | 74.2 |
| I* | 3667 | 31.28 | 1.93 | 3266 | 29.89 | 2.22 | 14.9 | 0.24 | 0.0 | 4.7 | 4.8 | 90.5 |
| J | 6150 | 30.69 | 1.98 | 5753 | 30.01 | 2.13 | 8.5 | 0.23 | 0.0 | 3.5 | 10.6 | 85.9 |

*Contains 8.9% BaO

TABLE V
SYNGAS TO HYDROCARBONS WITH COPPER CHROMITE CATALYSTS

| Catalyst | Temp., °F. | Pressure psig | Inlet GHSV | Inlet vol. % CO | Inlet vol. % $CO_2$ | Outlet GHSV | Outlet vol. % CO | Outlet vol. % $CO_2$ | CO Conversion, % |
|---|---|---|---|---|---|---|---|---|---|
| H | 575 | 1500 | 5185 | 29.29 | 5.16 | 3347 | 20.84 | 9.75 | 54.1 |
| I | 575 | 1500 | 4458 | 29.32 | 5.17 | 3038 | 23.64 | 9.31 | 45.0 |
| K* | 570 | 1000 | 4495 | 28.93 | 1.85 | 3223 | 25.38 | 4.75 | 37.1 |
|  | 570 | 1250 | 4332 | 27.63 | 4.84 | 2962 | 17.34 | 10.01 | 57.1 |
| L* | 540 | 1250 | 4703 | 30.69 | 5.46 | 3689 | 27.24 | 7.66 | 30.4 |
|  | 540 | 1500 | 4643 | 30.13 | 5.30 | 3566 | 25.68 | 7.98 | 34.5 |
|  | 575 | 1500 | 4643 | 30.13 | 5.30 | 3594 | 20.15 | 10.09 | 52.3 |

| Catalyst | Yield g/hr/g cat MeOH | Yield g/hr/g cat Hydrocarbons | Selectivity $CO_2$ | Selectivity MeOH | Selectivity Hydrocarbons | Schultz-Flory Coefficient |
|---|---|---|---|---|---|---|
| H | 0.687 | 0.176 | 7.2 | 58.6 | 34.2 | 0.46 |
| I | 0.576 | 0.084 | 8.9 | 68.4 | 22.7 | 0.46 |
| K* | 0.363 | 0.099 | 14.5 | 52.7 | 32.8 | 0.43 |
|  | 0.29 | 0.25 | 12.7 | 29.7 | 56.6 | 0.44 |
| L* | 0.25 | 0.15 | 5.9 | 40.0 | 54.1 | 0.44 |
|  | 0.24 | 0.17 | 8.0 | 34.2 | 57.8 | 0.45 |
|  | 0.22 | 0.31 | 11.7 | 20.8 | 67.5 | 0.45 |

*Contains <1 wt. % $K_2O$.

EXAMPLE 4

Synthesis of Higher ($C_2+$) Alcohols with Copper Chromite Catalysts

Catalyst M 82.0 g of $(NH_4)_2CrO_4$ was partially dissolved in 80 ml $H_2O$. Separately, 25.0 g $Cu(NO_3)_2.3H_2O$ was dissolved in 25 ml $H_2O$. The two solutions were rapidly mixed and the resulting brown precipitate was filtered and washed with 25 ml $H_2O$. The catalyst was dried and further heated to 250° F. The temperature wa raised to 375° F. for 1 hour and again raised to 425° F. for half an hour. To 17.5 g of the black catalyst was added 2 0 g $K_2CO_3$ dissolved in 17 ml $H_2O$. The catalyst was dried and calcined at 425° F. for 2 hours.

Testing Procedure

Catalyst M was tested for alcohol synthesis in a fixed-bed, continuous-flow pilot plant under the conditions shown in Table VI for 75 days. Yields were determined by gas chromatography. The flow rate was controlled by mass flow controllers and metered from the test unit by a wet test meter. The gas flow rate (cc of gas per gram of catalyst per hour) and carbon monoxide analysis were determined prior to reaction and again at the reaction temperature. Carbon monoxide conversion was determined for each 24 hour period. The liquid products were collected at constant operating conditions for about 24 to 125 hours and analyzed by gas chromatography. Several liquid samples were tested for water content (percent) by Karl Fischer analysis.

The results for higher alcohol synthesis with Catalyst M are given in Table VI. Higher ($C_2+$) alcohols were synthesized at reaction pressures from 1000 psig to 2000 psig. Reaction temperatures ranged from 620° F. to 680° F. Selectivities of $C_2+$ alcohols in the liquid product ranged from 15 wt. % to 30 wt. % depending on the reaction conditions. The crude alcohol product was periodically analyzed for $H_2O$ and found to contain less than 3 wt. % $H_2O$ in all samples tested. The catalyst remained active in this test which lasted 75 days.

Example 2 (see Table III) demonstrated the synthesis of higher alcohols with alkalized copper chromite catalysts.

TABLE VI
SYNGAS TO HIGHER ALCOHOLS WITH ALKALI COPPER CHROMITE

| Catalyst | | | | | | | | | | | | | | | | |
|---|---|---|---|---|---|---|---|---|---|---|---|---|---|---|---|---|
| Temp., °F. | 620 | 620 | 620 | 620 | 620 | 620 | 620 | 620 | 620 | 645 | 645 | 645 | 645 | 645 | 645 | 620 | 620 |
| Pressure, psig | 2000 | 2000 | 2000 | 2000 | 2000 | 2000 | 2000 | 2000 | 2000 | 2000 | 2000 | 2000 | 2000 | 2000 | 2000 | 1500 | 1500 |
| Day | 2 | 5 | 6 | 7 | 8 | 9 | 12 | 16 | 19 | 20 | 21 | 22 | 23 | 26 | 27 | 30 | 33 |
| Inlet | | | | | | | | | | | | | | | | | |
| GHSV, hr⁻¹ | 3742.9 | 3742.9 | 3742.9 | 3742.9 | 1873.9 | 1873.9 | 1873.9 | 1877.5 | 1877.5 | 1877.5 | 1877.5 | 1877.5 | 1877.5 | 1890.1 | 1890.1 | 1911.7 | 1911.7 |
| vol. % CO | 32.68 | 32.68 | 32.68 | 32.68 | 33.58 | 33.58 | 33.58 | 49.39 | 49.39 | 49.39 | 49.39 | 49.39 | 49.39 | 33.33 | 33.33 | 33.30 | 33.30 |
| vol. % CO₂ | 2.00 | 2.00 | 2.00 | 2.00 | 2.05 | 2.05 | 2.05 | 2.96 | 2.96 | 2.96 | 2.96 | 2.96 | 2.96 | 2.03 | 2.03 | 2.04 | 2.04 |
| Outlet | | | | | | | | | | | | | | | | | |
| GHSV, hr⁻¹ | 3290.4 | 3516.5 | 3505.8 | 3490.4 | 1596.1 | 1624.9 | 1686.5 | 1666.6 | 1756.9 | 1672.8 | 1692.9 | 1719.7 | 1741.6 | 1649.1 | 1625.9 | 1793.0 | 1777.1 |
| vol. % CO | 30.70 | 30.95 | 30.76 | 30.36 | 30.16 | 30.35 | 30.00 | 47.74 | 46.42 | 46.14 | 46.52 | 46.66 | 46.17 | 28.36 | 28.62 | 31.74 | 31.39 |
| vol. % CO₂ | 3.45 | 3.15 | 3.10 | 3.11 | 4.54 | 4.50 | 4.55 | 5.44 | 5.18 | 6.44 | 6.17 | 6.20 | 6.14 | 5.82 | 5.82 | 3.35 | 3.44 |
| Selectivity, wt. % | | | | | | | | | | | | | | | | | |
| CO₂ | 18.1 | 26.4 | 23.3 | 20.6 | 23.0 | 25.5 | 31.1 | 26.7 | 31.7 | 33.6 | 35.0 | 40.9 | 41.7 | 35.5 | 28.8 | 31.2 | 28.1 |
| MeOH | 41.7 | 55.4 | 40.1 | 65.4 | 56.1 | 57.5 | 40.7 | 52.6 | 44.2 | 43.5 | 42.5 | 36.5 | 33.4 | 32.1 | 42.6 | 42.6 | 53.6 |
| C₂⁺ Alcohol | 6.7 | 16.4 | 23.8 | 13.0 | 18.9 | 15.0 | 27.2 | 19.6 | 23.6 | 19.7 | 19.3 | 21.6 | 20.3 | 30.8 | 22.3 | 22.2 | 17.3 |
| Hydrocarbons | 33.4 | 1.8 | 12.8 | 1.0 | 2.0 | 2.0 | 1.0 | 1.1 | 0.5 | 3.2 | 3.2 | 1.0 | 4.6 | 1.6 | 6.3 | 4.0 | 1.0 |
| CO Conversion, % | 17.4 | 11.0 | 11.8 | 13.4 | 23.5 | 21.6 | 19.6 | 14.2 | 12.1 | 16.8 | 15.1 | 13.5 | 13.3 | 25.8 | 26.1 | 10.6 | 12.4 |
| Yield, g/hr/g cat | | | | | | | | | | | | | | | | | |
| Hydrocarbons | .045 | .002 | .012 | .001 | .002 | .002 | .001 | .001 | .001 | .003 | .003 | .001 | .004 | .002 | .007 | .002 | .001 |
| MeOH | .127 | .107 | .083 | .153 | .119 | .111 | .072 | .071 | .071 | .096 | .085 | .065 | .059 | .074 | .100 | .041 | .060 |
| C₂⁺ Alcohol | .013 | .023 | .035 | .022 | .029 | .021 | .034 | .027 | .027 | .031 | .028 | .028 | .028 | .051 | .038 | .015 | .014 |
| Wt % C₂⁺ Alcohol (In Liquid) | — | — | 13.6 | 16.5 | 17.9 | 17.9 | 17.9 | 23.8 | 23.8 | 29.5 | 29.5 | 29.5 | 29.5 | 29.9 | 25.6 | 18.2 | 18.2 |

| Catalyst | | | | | | | | | | | M | | | | | |
|---|---|---|---|---|---|---|---|---|---|---|---|---|---|---|---|---|
| Temp., °F. | 640 | 640 | 640 | 650 | 650 | 650 | 650 | 645 | 645 | 645 | 645 | 645 | 645 | 645 | 645 | 645 |
| Pressure, psig | 1500 | 1500 | 1500 | 1000 | 1000 | 1000 | 1000 | 1750 | 1750 | 1750 | 1750 | 1750 | 1750 | 1750 | 1750 | 1750 |
| Day | 34 | 35 | 36 | 40 | 41 | 42 | 44 | 47 | 48 | 49 | 50 | 51 | 54 | 56 | 61 | 62 |
| Inlet | | | | | | | | | | | | | | | | |
| GHSV, hr⁻¹ | 1911.7 | 1911.7 | 1911.7 | 1889.8 | 1889.8 | 1889.8 | 1907.9 | 1907.9 | 1907.9 | 1907.9 | 1907.9 | 1907.9 | 1907.9 | 2001.8 | 2001.8 | 2001.8 |
| vol. % CO | 33.30 | 33.30 | 33.30 | 33.05 | 33.05 | 33.05 | 32.41 | 32.41 | 32.41 | 32.41 | 32.41 | 32.41 | 32.41 | 33.64 | 33.64 | 33.64 |
| vol. % CO₂ | 2.04 | 2.04 | 2.04 | 2.01 | 2.01 | 2.01 | 1.97 | 1.97 | 1.97 | 1.97 | 1.97 | 1.97 | 1.97 | 2.13 | 2.13 | 2.13 |
| Outlet | | | | | | | | | | | | | | | | |
| GHSV, hr⁻¹ | 1722.2 | 1717.1 | 1741.5 | 1795.5 | 1799.8 | 1809.6 | 1650.9 | 1643.8 | 1534.4 | 1521.3 | 1460.8 | 1666.0 | 1685.5 | 1707.6 | 1786.0 | 1770.2 |
| vol. % CO | 30.47 | 30.78 | 30.59 | 31.11 | 31.13 | 31.19 | 28.35 | 28.60 | 28.46 | 28.42 | 27.87 | 28.05 | 29.23 | 30.33 | 30.30 | 30.61 |
| vol. % CO₂ | 4.07 | 3.95 | 3.99 | 3.08 | 3.30 | 3.30 | 5.16 | 4.46 | 4.45 | 4.63 | 4.64 | 4.61 | 4.81 | 4.76 | 4.16 | 4.29 |
| Selectivity, wt. % | | | | | | | | | | | | | | | | |
| CO₂ | 34.3 | 26.7 | 29.4 | 26.2 | 33.3 | 36.1 | 31.7 | 24.1 | 16.9 | 17.7 | 14.3 | 26.0 | 34.6 | 24.9 | 23.9 | 24.3 |
| MeOH | 47.5 | 52.7 | 45.2 | 49.4 | 48.6 | 45.3 | 49.5 | 46.1 | 56.1 | 48.5 | 54.8 | 46.3 | 39.3 | 49.4 | 50.9 | 46.9 |
| C₂⁺ Alcohol | 16.8 | 18.8 | 23.8 | 23.4 | 16.6 | 17.5 | 17.5 | 28.8 | 26.0 | 31.9 | 29.3 | 24.7 | 23.9 | 24.7 | 24.2 | 25.4 |
| Hydrocarbons | 1.4 | 1.8 | 1.6 | 1.0 | 1.5 | 1.1 | 1.2 | 1.0 | 1.0 | 1.5 | 1.6 | 3.0 | 2.2 | 1.0 | 1.0 | 3.4 |
| CO Conversion, % | 15.2 | 17.0 | 16.3 | 10.6 | 10.3 | 9.6 | 24.3 | 24.0 | 29.4 | 34.2 | 34.2 | 24.4 | 20.3 | 23.1 | 19.6 | 20.4 |
| Yield, g/hr/g cat | | | | | | | | | | | | | | | | |
| Hydrocarbons | .001 | .001 | .001 | .001 | .001 | .001 | .001 | .000 | .001 | .002 | .002 | .003 | .002 | .001 | .001 | .003 |
| MeOH | .066 | .081 | .067 | .047 | .045 | .039 | .106 | .098 | .146 | .165 | .165 | .100 | .071 | .110 | .096 | .092 |
| C₂⁺ Alcohol | .017 | .021 | .025 | .016 | .011 | .011 | .027 | .044 | .049 | .064 | .064 | .038 | .031 | .039 | .033 | .036 |
| Wt % C₂⁺ Alcohol (In Liquid) | 19.0 | 19.0 | 19.0 | 23.2 | 23.2 | 23.2 | 20.1 | 27.8 | 27.8 | 27.8 | 27.8 | 27.8 | 24.8 | 21.8 | 21.8 | 20.1 |

TABLE VI-continued
SYNGAS TO HIGHER ALCOHOLS WITH ALKALI COPPER CHROMITE

| Catalyst | | | | | | M | | | | |
|---|---|---|---|---|---|---|---|---|---|---|
| Temp., °F. | 645 | 645 | 680 | 680 | 645 | 645 | 680 | 680 | 680 |
| Pressure, psig | 1750 | 1750 | 1750 | 1750 | 1750 | 1750 | 1750 | 1750 | 1750 |
| Day | 64 | 65 | 68 | 69 | 70 | 71 | 72 | 73 | 75 |
| Inlet | | | | | | | | | |
| GHSV, hr$^{-1}$ | 2001.8 | 2001.8 | 2001.8 | 2001.8 | 2001.8 | 2001.8 | 2001.8 | 2001.8 | 2001.8 |
| vol. % CO | 33.64 | 33.64 | 33.64 | 33.64 | 33.64 | 33.64 | 33.64 | 33.64 | 33.64 |
| vol. % CO$_2$ | 2.13 | 2.13 | 2.13 | 2.13 | 2.13 | 2.13 | 2.13 | 2.13 | 2.13 |
| Outlet | | | | | | | | | |
| GHSV, hr$^{-1}$ | 1778.9 | 1802.0 | 1708.2 | 1715.7 | 1715.6 | 1733.4 | 1697.2 | 1711.7 | 1730.5 |
| vol. % CO | 30.57 | 30.50 | 28.40 | 29.14 | 28.81 | 29.13 | 29.07 | 28.89 | 29.09 |
| vol. % CO$_2$ | 4.33 | 4.33 | 5.70 | 5.60 | 5.52 | 5.51 | 5.27 | 5.13 | 5.23 |
| Selectivity, wt. % | | | | | | | | | |
| CO$_2$ | 26.5 | 28.9 | 29.1 | 30.8 | 29.1 | 31.4 | 26.0 | 25.3 | 28.2 |
| MeOH | 56.6 | 46.1 | 45.8 | 23.9 | 23.3 | 18.5 | 53.5 | 41.0 | 39.4 |
| C$_2^1$ Alcohol | 15.3 | 23.8 | 23.9 | 24.0 | 35.2 | 41.5 | 13.6 | 23.7 | 22.8 |
| Hydrocarbons | 1.6 | 1.2 | 1.2 | 21.2 | 12.4 | 8.6 | 6.9 | 10.0 | 9.6 |
| CO Conversion, % | 19.2 | 18.8 | 28.0 | 25.8 | 26.6 | 25.0 | 26.7 | 26.6 | 25.3 |
| Yield, g/hr/g cat | | | | | | | | | |
| Hydrocarbons | .002 | .001 | .001 | .023 | .014 | .009 | .008 | .011 | .010 |
| MeOH | .105 | .082 | .123 | .059 | .060 | .045 | .137 | .105 | .096 |
| C$_2^1$ Alcohol | .020 | .030 | .046 | .043 | .065 | .072 | .025 | .044 | .040 |
| Wt % C$_2^1$ Alcohol (In Liquid) | 20.1 | 20.1 | 25.9 | 25.9 | 27.6 | 27.6 | 27.6 | 27.6 | 27.6 |

EXAMPLE 5

Composition of Catalysts

Catalysts H through I were analyzed for copper and chromium content and surface area. The results are given in Table VII.

TABLE VII

COPPER CHROMITE SYNGAS CATALYST COMPOSITION

| Catalyst | Analysis (Wt %) | | | Surface Area |
|---|---|---|---|---|
| | CuO | $Cr_2O_3$ | Other | ($m^2/g$) |
| H | 46.8 | 53.2 | | 23 |
| I | 39.9 | 51.2 | 8.9* | 23 |
| J | 42.8 | 57.2 | | 24 |
| K | 53.4 | 45.6 | 1.0** | 65 |
| L | 50.5 | 48.5 | 1.0** | 37 |
| M | 36.8 | 56.7 | 6.5** | N/A |

*BaO
**$K_2O$
N/A = not available

The foregoing detailed description is given for clearness of understanding only, and no unnecessary limitations should be understood therefrom, as modifications within the scope of the invention will be apparent to those skilled in the art.

We claim:

1. A process for converting synthesis gas comprising a mixture of carbon monoxide and hydrogen to a product selected from the group consisting of n-paraffins and higher alcohols, said process comprising the step of contacting said synthesis gas under synthesis gas conversion conditions including a temperature in the range of about 500° F. to about 700° F. and a pressure of about 500 psig to about 1500 psig for the production of n-paraffins or greater than about 1500 psig to about 2000 psig for the production of higher alcohols with a copper chromite conversion catalyst whereby sad synthesis gas is converted to a n-paraffins or higher alcohols, wherein said catalyst prior to reduction at synthesis gas conversion conditions consists essentially of a non-stoichoimetric mixed copper-chromium oxide containing less than about 1 wt. % of an alkali metal compound (measured as carbonate) for the production of n-paraffins or about 1 wt. % or more of an alkali metal compound (measured as carbonate) for the production of higher alcohols, said catalyst being prepared by the method comprising the steps of:
   (a) coprecipitating copper (II) ions with chromate ions by mixing respective aqueous solutions of a copper (II) salt and ammonium chromate containing a molar excess of ammonium relative to copper to produce a copper-ammonium-chromate precipitate;
   (b) drying said copper-ammonium-chromate precipitate;
   (c) calcining said dried copper-ammonium-chromate precipitate at a sufficiently high temperature no greater than about 700° F. to produce a stable copper chromite catalyst, said temperature being insufficiently high to degrade said copper chromite catalyst; and
   (d) introducing said alkali metal compound to said catalyst during preparation.

2. The process of claim 1 wherein said copper and chromate ions of step (a) are present in respective amounts to provide a copper chromite catalyst having a $CuO:Cr_2O_3$ weight ratio in the range of about 0.5:1 to about 1.5:1.

3. The process of claim 1 wherein said respective solutions comprise copper nitrate and ammonium chromate in a weight ratio of ammonium chromate to copper nitrate of at least about 3:1.

4. The process of claim 1 wherein said ammonium chromate solution comprises a soluble ammonium salt in addition to ammonium chromate.

5. The process of claim 4 wherein said additional soluble ammonium salt is ammonium hydroxide.

6. The process of claim 1 wherein said ammonium chromate solution comprises a soluble alkali metal chromate in addition to ammonium chromate.

7. The process of claim 1 wherein said calcining step (c) is carried out at a temperature of no greater than about 575° F.

8. The process of claim 7 wherein said calcining step (c) is carried out at no greater than about 525° F.

9. The process of claim 1 wherein said precipitate of step (a) is washed to remove soluble unreacted materials and byproducts prior to drying and calcining.

10. The process of claim 1 wherein said synthesis gas comprises about 2 to about 20 vol. % $CO_2$.

11. The process of claim 1 wherein said synthesis gas conversion reaction is carried out at a pressure of at least about 500 psig.

12. A process for producing n-paraffins according to claim 1 wherein said catalyst comprises less than about 1 wt. % of said alkali metal compound (measured as carbonate).

13. The process of claim 12 wherein said conversion reaction is carried out at a temperature of about 525° C. to about 600° F. and at a pressure of about 500 psig to about 1500 psig to produce n-paraffins.

14. The process of claim 1 wherein said alkali metal compound is introduced to said catalyst by
   (e) impregnating said copper chromite catalyst with a solution of said alkali metal compound; and
   (f) drying said alkali metal compound-impregnated copper chromite catalyst by calcining.

15. The process of claim 14 wherein said alkali metal compound is selected from the group consisting of $K_2CO_3$ and KOH.

16. The process of claim 14 wherein said drying step (f) is carried out at a temperature of up to about 650° F.

17. A process for producing higher alcohols according to claim 14 wherein said catalyst comprises about 1 wt. % to about 10 wt. % of said alkali metal compound (calculated as carbonate).

18. The process of claim 17 wherein said synthesis gas conversion is carried out at a temperature in the range of about 550° F. to about 700° F. and a pressure of greater than about 1500 psig to produce higher alcohols.

19. The process of claim 18 wherein said conversion reaction pressure is between about 1750 psig and about 2000 psig.

20. A process for converting synthesis gas comprising a mixture of carbon monoxide and hydrogen to a product selected from the group consisting of n-paraffins and higher alcohols, said process comprising the step of contacting said synthesis gas with a copper chromite conversion catalyst at a temperature in the range of about 500° F. to about 700° F. and a pressure of about 500 psig to about 1500 psig for the production of n-paraffins or greater than about 1500 psig to about 2000 psig for the production of higher alcohols, wherein said catalyst prior to reduction at synthesis gas conversion conditions consists essentially of a non-stoichiometric mixed copper-chromium oxide containing less than about 1 wt. % of an alkali metal compound (measured as carbonate) for the production of n-paraffins or about 1 wt. % or more of an alkali metal compound (measured as carbonate) for the production of higher alcohols, said catalyst being prepared by the method comprising the steps of:

(a) coprecipitating copper (II) ions with chromate ions in the presence of a molar excess of ammonium relative to copper by mixing respective aqueous solutions of a copper (II) salt and ammonium chromate to produce a copper-ammonium-chromate precipitate;

(b) drying said copper-ammonium-chromate precipitate;

(c) calcining said dried copper-ammonium-chromate precipitate at a sufficiently high temperature no greater than about 575° F. to produce a stable copper chromite catalyst, said temperature being insufficiently high to degrade said copper chromite catalyst, said copper and chromate ions of step (a) being present in respective amounts to provide a copper chromite catalyst having a $CuO:Cr_2O_3$ weight ratio in the range of about 0.5:1 to about 1.5:1 and, (d) introducing said alkali metal compound to said catalyst during preparation.

21. The process of claim 20 wherein said ammonium chromate solution comprises a soluble ammonium salt in addition to ammonium chromate.

22. The process of claim 20 wherein said ammonium chromate solution comprises a soluble alkali metal chromate in addition to ammonium chromate.

23. The process of claim 20 wherein said respective solutions of step (a) comprise copper nitrate and ammonium chromate in a weight ratio of ammonium chromate to copper nitrate of at least about 3:1.

24. The process of claim 20 wherein said precipitate of step (a) is washed to remove soluble unreacted materials and byproducts prior to drying and calcining.

25. The process of claim 20 wherein said synthesis gas comprises about 2 to about 20 vol. % $CO_2$.

26. A process for producing n-paraffins according to claim 20 wherein said catalyst comprises less than about 1 wt. % of said alkali metal compound (measured as carbonate).

27. The process of claim 26 wherein said conversion reaction is carried out at a temperature of about 525° F. to about 600° F. and at a pressure of about 500 psig to about 1500 psig to produce n-paraffins.

28. The process of claim 20 wherein said catalyst preparation method includes the steps of:

(e) impregnating said copper chromite catalyst with a solution of an alkali metal compound; and, (f) drying said alkali metal compound-impregnated copper chromite catalyst by calcining at a temperature of up to about 650° F.

29. A process for producing higher alcohols according to claim 28 wherein said catalyst comprises about 1 wt. % to about 10 wt. % of said alkali metal compound (calculated as carbonate) after said impregnating and drying steps (e) and (f).

30. The process of claim 29 wherein said synthesis gas conversion is carried out at a temperature in the range of about 550° F. to about 700° F. and a pressure of greater than about 1500 psig to produce higher alcohols.

31. A process for converting synthesis gas comprising a mixture of carbon monoxide and hydrogen and up to about 20 vol. % carbon dioxide to a product selected from the group consisting of n-paraffins and higher alcohols, said process comprising the step of contacting said synthesis gas with a copper chromite conversion catalyst at a temperature in the range of about 500° F. to about 700° F. and a pressure of about 500 psig to about 1500 psig for the production of n-paraffins or greater than about 1500 psig to about 2000 psig for the production of higher alcohols whereby said synthesis gas is converted to n-paraffins or higher alcohols respectively, which catalyst prior to reduction at synthesis gas conversion conditions consists essentially of a non-stoichiometric mixed copper-chromium oxide containing less than about 1 wt. % of an alkali metal compound (measured as carbonate) for the production of n-paraffins or about 1 wt. % or more of an alkali metal compound (measured as carbonate) for the production of higher alcohols, said catalyst being prepared by the method comprising the steps of:

(a) coprecipitating copper (ii) ions with chromate ions in the presence of a molar excess of ammonium relative to copper by mixing respective aqueous solutions of copper nitrate and ammonium chromate in a weight ratio of ammonium chromate to copper nitrate of at least about 3:1 to produce a copper-ammonium-chromate precipitate, said ammonium chromate solution comprising at least one member of the group consisting of soluble ammonium salts and soluble alkali metal chromates in addition to ammonium chromate;

(b) washing said copper-ammonium-chromate precipitate to remove soluble reacted materials and byproducts;

(c) drying said washed copper-ammonium-chromate precipitate;

(d) calcining said dried copper-ammonium-chromate precipitate at a sufficiently high temperature no greater than about 575° F. to product a stable copper chromite catalyst, said temperature being insufficiently high to degrade said copper chromite catalyst, said copper and chromate ions of step (a) being present in respective amounts to provide a copper chromite catalyst having a $CuO:Cr_2O_3$ weight ratio in the range of about 0.5:1 to about 1.5:1; and, (e) introducing said alkali metal compound to said catalyst during preparation.

32. A process for producing n-paraffins according to claim 31 wherein said catalyst comprises less than about 1 wt. % of said alkali metal compound (measured as carbonate).

33. The process of claim 31 wherein said conversion reaction is carried out at a temperature of about 525° F. to about 600° F. and at a pressure of about 500 psig to about 1500 psig to produce n-paraffins.

34. A process for producing higher alcohols according to claim 31 wherein said catalyst preparation method includes the steps of:

(f) impregnating said copper chromite catalyst with a solution of an alkali metal compound; and, (g) drying said alkali metal compound-impregnated copper chromite catalyst by calcining at a temperature of up to about 650° F., the amount of said alkali metal compound being sufficient to provide about 1 wt. % to about 10 wt. % of said alkali metal compound (calculated as carbonate) in said catalyst after said impregnating and drying steps (f) and (g).

35. The process of claim 34 wherein said synthesis gas conversion is carried out at a temperature in the range of about 550° F. to about 700° F. and a pressure of greater than about 1500 psig to produce higher alcohols.

* * * * *